(12) United States Patent
Gill

(10) Patent No.: US 12,200,822 B2
(45) Date of Patent: Jan. 14, 2025

(54) INDUCTION HEATING ASSEMBLY FOR A VAPOUR GENERATING DEVICE

(71) Applicant: JT International S.A., Geneva (CH)

(72) Inventor: Mark Gill, London (GB)

(73) Assignee: JT International S.A. (CH)

( * ) Notice: Subject to any disclaimer, the term of this patent is extended or adjusted under 35 U.S.C. 154(b) by 587 days.

(21) Appl. No.: 16/760,767

(22) PCT Filed: Dec. 28, 2018

(86) PCT No.: PCT/EP2018/097075
§ 371 (c)(1),
(2) Date: Apr. 30, 2020

(87) PCT Pub. No.: WO2019/129846
PCT Pub. Date: Jul. 4, 2019

(65) Prior Publication Data
US 2021/0076743 A1   Mar. 18, 2021

(30) Foreign Application Priority Data

Dec. 29, 2017  (EP) ..................................... 17211202
Dec. 22, 2018  (TW) .................................. 107146643

(51) Int. Cl.
*A24F 13/00*   (2006.01)
*A24F 40/465*  (2020.01)
(Continued)

(52) U.S. Cl.
CPC ........... *H05B 1/023* (2013.01); *A24F 40/465* (2020.01); *A24F 40/51* (2020.01); *A24F 40/57* (2020.01);
(Continued)

(58) Field of Classification Search
CPC ....................................................... A24F 47/00
(Continued)

(56) References Cited

U.S. PATENT DOCUMENTS 10,791,760 B2 *  10/2020  Zuber .................. H05B 1/0244
2003/0033055 A1   2/2003  McRae et al.
(Continued)

FOREIGN PATENT DOCUMENTS

CN          1072262 A    5/1993
CN        106998959 A    8/2017
(Continued)

OTHER PUBLICATIONS

International Search Report Including Written Opinion for PCT/EP2018/097075 mailed Mar. 29, 2019; 16 pages.
(Continued)

*Primary Examiner* — Phuong K Dinh
(74) *Attorney, Agent, or Firm* — Lerner David LLP

(57) ABSTRACT

An induction heating assembly for a vapour generating device includes an induction heating device and an electronic component having material able to act as a first susceptor, wherein the induction heating device is arranged to heat, in use, a second susceptor for a first period, and the electronic component is arranged to be activated for a second period, and wherein the first period and the second period are non-concurrent. This achieves reduced interference in the functionality of the electronic component.

17 Claims, 3 Drawing Sheets

(51) Int. Cl.
*A24F 40/51* (2020.01)
*A24F 40/57* (2020.01)
*H05B 1/02* (2006.01)
*H05B 6/06* (2006.01)
*H05B 6/10* (2006.01)
*A24F 40/20* (2020.01)

(52) U.S. Cl.
CPC ............... *H05B 6/06* (2013.01); *H05B 6/108* (2013.01); *A24F 40/20* (2020.01)

(58) Field of Classification Search
USPC .................................................. 131/328–329
See application file for complete search history.

(56) References Cited

U.S. PATENT DOCUMENTS

| | | |
|---|---|---|
| 2015/0320116 A1 | 11/2015 | Bleloch et al. |
| 2016/0150825 A1 | 6/2016 | Mironov et al. |
| 2017/0027233 A1* | 2/2017 | Mironov ............... H05B 1/0244 |
| 2017/0055584 A1 | 3/2017 | Blandino et al. |
| 2017/0203377 A1 | 7/2017 | Yokoyama et al. |
| 2017/0251718 A1 | 9/2017 | Armoush et al. |
| 2018/0043114 A1 | 2/2018 | Bowen et al. |
| 2021/0145071 A1* | 5/2021 | Butin ........................ A24D 1/20 |

FOREIGN PATENT DOCUMENTS

| | | |
|---|---|---|
| CN | 107105779 A | 8/2017 |
| CN | 107112247 A | 8/2017 |
| JP | 2002190374 A | 7/2002 |
| JP | 2013109940 A | 6/2013 |
| TW | 201609005 A | 3/2016 |
| TW | 201733406 A | 9/2017 |
| WO | 0119141 A1 | 3/2001 |
| WO | 2016075436 A1 | 5/2016 |
| WO | 2019002613 A1 | 1/2019 |

OTHER PUBLICATIONS

Search Report dated Aug. 21, 2022 from the Office Action for Taiwanese Application No. 107146643 issued Aug. 22, 2022, 1 page.

Search Report dated Oct. 11, 2022 from the Office Action for Chinese Application No. 201880084762.0 issued Oct. 18, 2022 pp. 1-3.

* cited by examiner

INDUCTION HEATING ASSEMBLY FOR A VAPOUR GENERATING DEVICE

CROSS-REFERENCE TO RELATED APPLICATIONS

The present application is a national phase entry under 35 U.S.C. § 371 of International Application No. PCT/EP2018/097075, filed Dec. 28, 2018, published in English, which claims priority to European Application No. 17211202.1 filed Dec. 29, 2017 and to Taiwanese Application No. 107146643 filed Dec. 22, 2018, all of the disclosures of which are incorporated herein by reference.

BACKGROUND

The present invention relates to an induction heating assembly for a vapour generating device.

Devices which heat, rather than burn, a substance to produce a vapour for inhalation have become popular with consumers in recent years.

Such devices can use one of a number of different approaches to provide heat to the substance. One such approach is that of simple provision of a heating element to which electrical power is provided to heat the element, the element in turn heating the substance to generate vapour.

One way to achieve such vapour generation is to provide a vapour generating device which employs an inductive heating approach. In such a device an inductions coil (hereinafter also referred to as an inductor and induction heating device) is provided with the device and a susceptor is provided with the vapour generation substance. Electrical energy is provided to the inductor when a user activates the device which in turn creates an electromagnetic (EM) field. The susceptor couples with the field and generates heat which is transferred to the substance and vapour is created as the substance is heated.

Using induction heating to generate vapour has the potential to provide controlled heating and therefore controlled vapour generation. However, in practice such an approach can result in unsuitable temperatures unknowingly being produced in the vapour generation substance. This can waste power making it expensive to operate and risks damaging components or making ineffective use of the vapour generation substance inconveniencing users who expect a simple and reliable device.

This has been previously addressed by monitoring temperatures in a device. Adequate temperature monitoring and/or control is also important because it prevents overheating or burning of the substance used to generate vapour.

However, the monitored temperatures have been found to be unreliable and not representative of the temperatures actually produced further reducing the reliability of such a device.

The present invention seeks to mitigate at least some of the above problems.

SUMMARY OF INVENTION

According to a first aspect, there is provided an induction heating assembly for a vapour generating device, the heating assembly comprising: an induction heating device and an electronic component having material able to act as a first susceptor, wherein the induction heating device is arranged to heat, in use, a second susceptor for a first period, and the electronic component is arranged to be activated for a second period, and wherein the first period and the second period are non-concurrent.

We have found that simultaneously operating the electronic component and the induction heating device can cause the electronic component not to function properly. This is due to the induction heating device causing interference in the electronic component. In other words, the electronic component may be susceptible to interference by excitation caused by operation of the induction heating device during use of the induction heating device. As such, by operating the induction heating device and the electronic component in non-concurrent periods the induction heating device and electronic component are able to function as desired without either having a detrimental effect on the functioning of the other.

The electronic component may be an LED indicator; a sensor arranged to detect presence of a consumable, such as a cartridge or an induction heatable body, in a heating chamber, such as a photo or light sensor; a battery monitor; or a sensor arranged to detect age of a consumable. Typically, the electronic component is a temperature sensor, the temperature sensor being arranged to monitor, in use, a temperature related to heat generated from the second susceptor for the second period.

We have found that the amount of noise in a signal output by the temperature sensor when the temperature sensor is used to monitor temperature due to the EM field generated by the induction heating device is able to be reduced by operating the temperature sensor at a different time to when the induction heating device is operated. This allows the temperature to be monitored to a greater level of accuracy and precision making the monitored temperature to be more representative of the true temperatures produced. This leads to an improvement in the reliability and safety of the device since the temperatures produced by the heating can be more reliably measured allowing any unsuitable temperatures to be addressed more easily and with a greater amount of certainty.

Of course, the induction heating device and the electronic component/temperature sensor may be separate or distinct components from each other.

The first and/or second susceptor may comprise one or more, but not limited to, of aluminium, iron, nickel, stainless steel and alloys thereof, e.g. nickel chromium. With the application of an electromagnetic field in its vicinity, the susceptor may generate heat due to eddy currents and magnetic hysteresis losses resulting in a conversion of energy from electromagnetic to heat.

While the first period and second period do not overlap, they may be arranged to occur in any possible way, such as with a gap between the first and second periods. Typically, the first and second period are arranged to be sequential.

We intend the term "sequential" to mean one substantially following the next, ideally without there being any gap or overlap between the first and second periods. This allows the monitored temperature to be as representative of the temperature achieved before or during heating by avoiding fluctuations in the ambient temperature around the induction heating assembly or cooling after the first period has finished causing a change in temperature before the second period starts or after the second period finishes. In particular, we have determined that the effects of the noise caused by the induction device heating the susceptor (i.e. the second susceptor) during the first period reduce very quickly once heating is stopped such that any gap or overlap between the first and second periods should ideally be as small as possible. Nonetheless, practical embodiments may include a small gap or overlap between the periods (e.g. of up to about 10 percent (%) of the duration of either or both of the first and second periods or of up to about 10 milliseconds (ms)) and still be considered to be sequential for the purposes of the present invention. Most preferably, however, any gap or overlap between the periods is less than 1% of the duration of either or both of the first and second periods or less than 1 ms.

Each period may occur only once in any one use of the induction heating assembly by a user. Typically however, the first period is arranged to be repeated at least once and/or the second period is arranged to be repeated at least once. This allows for multiple cycles of heating and/or temperature monitoring. This provides an improved accuracy of the temperature throughout the use of the induction heating assembly when the second period is repeated and less fluctuation in temperature over the use of the induction heating assembly when the first period is repeated.

Preferably, each of the first and second periods is arranged to be repeated at least once and the first and second periods are arranged to alternate. This improves how representative the monitored temperature is of the temperature achieved during the first period and further reduces fluctuations caused by providing applying and not applying heating.

One cycle of the first period and the second period may last any suitable period of time. Typically, the time from the start of one of the first or second period to the end of the other period is arranged to be about 0.05 seconds (s) to 0.15 seconds. This reduces inconvenience to a user of using the induction heating assembly by keeping the length of a single cycle shorter than the user's likely use the induction heating assembly, which is anticipated to be of the order of one or more seconds at any one time. Further, we have found that this period keeps a sufficient response speed for temperature monitoring, and at the same time gives the induction heating device sufficient time to effectively increase temperature. This is because a time shorter than 0.05 s would have a negative effect on the capability to increase the temperature, but a time longer than 0.15 s would negatively affect the speed of response able to be achieved when responding to the temperature monitoring by adapting the heating applied.

The first period may be arranged to be longer than the second period, or the first period may be arranged to be the same length of time as the second period, or the first period may be arranged to be shorter than the second period. The first period being longer than the second period is advantageous because it allows more time for heating allowing either a higher temperature to be achieved or for the heat to spread making the temperature more even across the volume being heated. This also reduces the amount of heat loss during the second period. The first period and the second period being the same length is advantageous because it simplifies operation of the induction heating assembly. The first period being shorter than the second period is advantageous because it allows more time for monitoring temperature relative to the amount of time spent heating.

The amount of heat provided by the induction heating device may be determined independently of the temperature monitored by the temperature sensor. Typically though, the induction heating device is arranged to adjust the amount of heat provided to the susceptor (i.e. the second susceptor) based on the temperature monitored by the temperature sensor. This allows the monitoring carried out by the temperature sensor to be used as feedback thereby allowing the heating to be adjusted to take account of fluctuations in the ambient or local temperature or different conditions in the environment in which the induction heating assembly is located.

The induction heating assembly may further comprise a controller arranged in use to control the induction heating device and temperature sensor. The controller may be arranged in use to control the induction heating device based on the temperature monitored by the temperature sensor. Preferably, the controller is arranged to control the induction heating device by being arranged in use to adjust the amount of power supplied to the induction heating device.

The controller may record and/or store and/or conduct processing on the monitored temperatures. Typically, the controller is configured to average temperatures monitored by the temperature sensor over a third period so as to allow noise detection in the temperature monitored by the temperature sensor. By allowing noise detection, additional noise can be removed from the signal produced by the temperature sensor when monitoring temperature. This would then allow the accuracy and precision of the monitored temperature to be improved. Preferably, the controller may be further configured to detect noise in the temperature monitored by the temperature sensor based on the averaged temperatures monitored during the third period and apply a filter to temperature monitored by the temperature sensor based on the detected noise so as to reduce noise in monitored temperatures.

The components of the induction heating assembly may be powered in any suitable manner. Typically, the induction heating assembly further comprises a power source arranged in use to provide power to the induction heating device and the temperature sensor. This allows the induction heating assembly to operate without an external supply of power.

The induction heating device may be provided in any form suitable for providing heating by induction. Typically, the induction heating device is an induction heating coil. This allows an EM field to be generated with a regular and predictable shape to allow heating to be provided in more predictable amounts in a more controllable manner.

The temperature sensor may be positioned at an axial centre of the induction coil, or at a position outside of the induction coil. Typically however, the temperature sensor is positioned between an axial end of the induction coil and a centre of the induction coil, preferably on a central longitudinal axis of the induction coil. Preferably, the temperature sensor may be positioned at an axial end of the induction coil. We have found that by locating the temperature sensor in this position a suitable balance is achieved between the ability to accurately measure temperature and reducing noise in the signal produced by the temperature sensor. Moving the temperature sensor beyond an axial end of the induction coil reduces the noise in the signal produced by the temperature sensor but reduces the accuracy of the temperature measurement since the temperature sensor is further from the location where the heat is produced. On the other hand, by locating the temperature sensor at the axial centre of the induction coil, the amount of noise is increased but the measured temperature has a greater likelihood of being representative of the temperature caused by the heating.

The assembly may be arranged to operate in use with a fluctuating electromagnetic field having a magnetic flux density of between approximately 0.5 T and approximately 2.0 T at the point of highest concentration.

The power source and circuitry may be configured to operate at a high frequency. Preferably, the power source and circuitry may be configured to operate at a frequency of between approximately 80 kHz and 500 kHz, preferably approximately 150 kHz and 250 kHz, more preferably approximately 200 kHz Whilst the induction coil may comprise any suitable material, typically the induction coil may comprise a Litz wire or a Litz cable.

According to a second aspect, there is provided a vapour generating device comprising: an induction heating assembly according to any one of the preceding claims; a heating compartment arranged to receive a body comprising a vaporisable substance and an induction heatable susceptor; an air inlet arranged to provide air to the heating compartment; and an air outlet in communication with the heating compartment. It is intended the induction heatable susceptor may be the "second susceptor" referred to above.

The vaporisable substance may be any type of solid or semi-solid material. Example types of vapour generating solids include powder, granules, pellets, shreds, strands, porous material or sheets. The substance may comprise plant derived material and in particular, the substance may comprise tobacco.

Preferably, the vaporisable substance may comprise an aerosol-former. Examples of aerosol-formers include poly-hyrdric alcohols and mixtures thereof such as glycerine or propylene glycol. Typically, the vaporisable substance may comprise an aerosol-former content of between approximately 5% and approximately 50% on a dry weight basis. Preferably, the vaporisable substance may comprise an aerosol-former content of approximately 15% on a dry weight basis.

Also, the vaporisable substance may be the aerosol-former itself. In this case, the vaporisable substance may be liquid. Also, in this case, the body may have a liquid retaining substance (e.g. a bundle of fibres, porous material such as ceramic, etc.) which retains the liquid to be vaporized by the vaporizer such as heater and allows a vapour to be formed and released/emitted from the liquid retaining substance towards the air outlet for inhalation by a user.

Upon heating, the vaporisable substance may release volatile compounds. The volatile compounds may include nicotine or flavour compounds such as tobacco flavouring.

The body may be a capsule which includes in use a vaporisable substance inside an air permeable shell. The air permeable material may be a material which is electrically insulating and non-magnetic. The material may have a high air permeability to allow air to flow through the material with a resistance to high temperatures. Examples of suitable air permeable materials include cellulose fibres, paper, cotton and silk. The air permeable material may also act as a filter. Alternatively, the body may be a vaporisable substance wrapped in paper. Alternatively, the body may be a vaporisable substance held inside a material that is not air permeable, but which comprises appropriate perforation or openings to allow air flow. Alternatively, the body may be the vaporisable substance itself. The body may be formed substantially in the shape of a stick.

According to a third aspect, there is provided a method of monitoring temperature in a vapour generating device, the method comprising: induction heating a body comprising a vaporisable substance and an induction heatable susceptor using an induction heating device; monitoring a temperature of the body, wherein heating and monitoring are conducted non-concurrently. It is intended the induction heatable susceptor may be the "second susceptor" referred to above.

BRIEF DESCRIPTION OF FIGURES

An example of an induction heating assembly is described in detail below, with reference to the accompanying figures, in which.

DETAILED DESCRIPTION

We now describe an example of a vapour generating device, including a description of an example induction heating assembly and an example induction heatable cartridge. An example method of monitoring temperature in a vapour generating device is also described.

Figure 1:
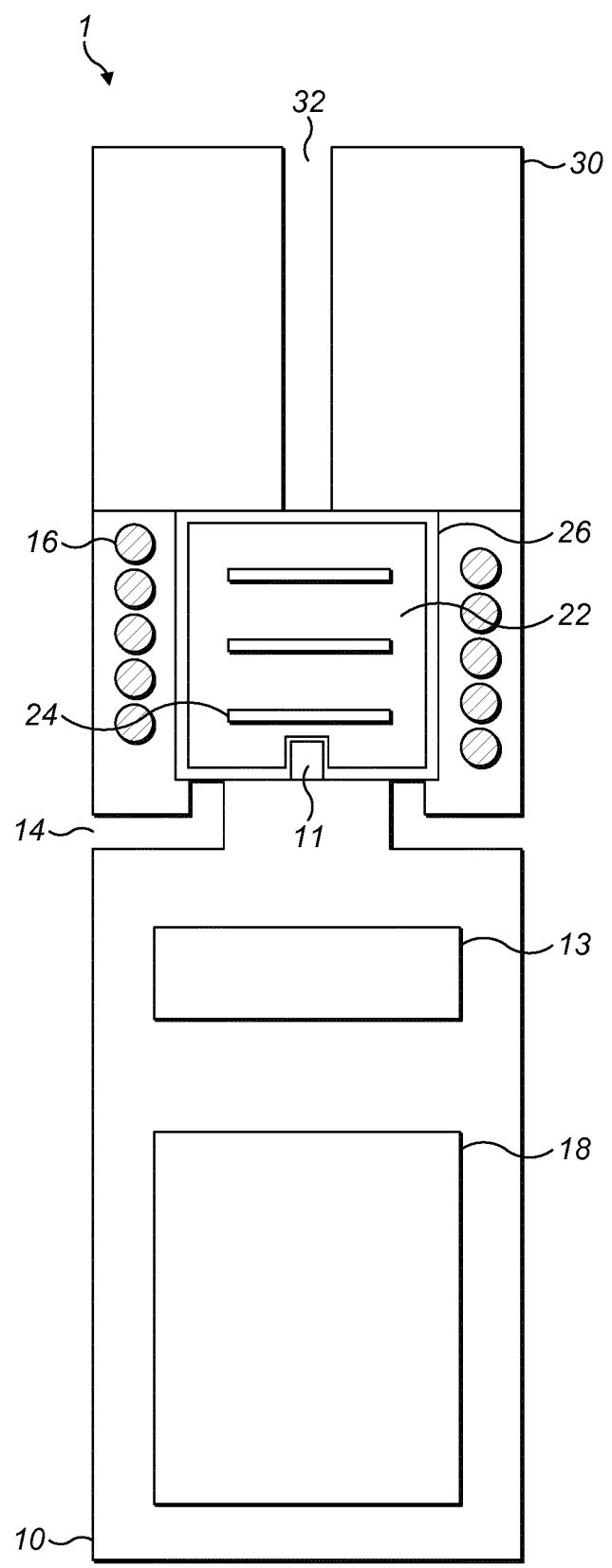
FIG. 1 shows a schematic view of an example vapour generating device.
Figure 2:
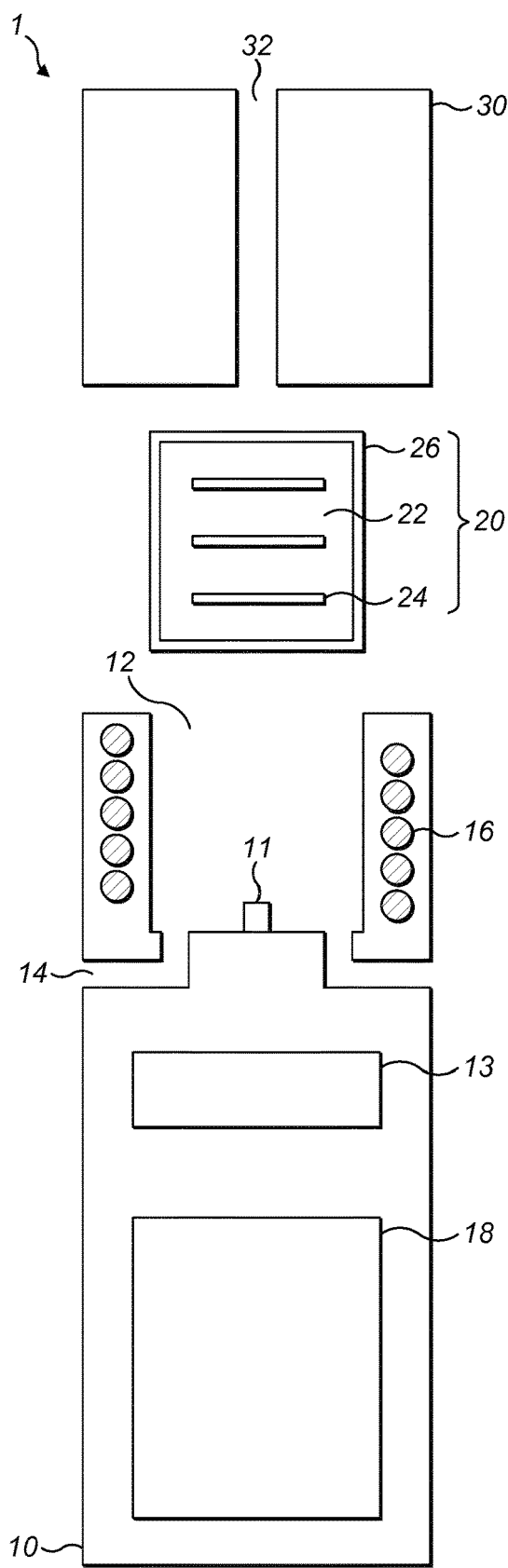
FIG. 2 shows an exploded view of the vapour generating device according to the example shown in FIG. 1.

Referring now to FIG. 1 and FIG. 2, an example vapour generating device is generally illustrated at 1 in an assembled configuration in FIG. 1 and an unassembled configuration in FIG. 2.

The example vapour generating device 1 is a hand held device (by which we intend to mean a device that a user is able to hold and support un-aided in a single hand), which has an induction heating assembly 10, an induction heatable cartridge 20 and a mouthpiece 30. Vapour is released by the cartridge when it is heated. Accordingly, vapour is generated by using the induction heating assembly to heat the induction heatable cartridge. The vapour is then able to be inhaled by a user at the mouthpiece.

In this example, a user inhales the vapour by drawing air into the device 1, through or around the induction heatable cartridge 20 and out of the mouthpiece 30 when the cartridge is heated. This is achieved by the cartridge being located in a heating compartment 12 defined by a portion of the induction heating assembly 10, and the compartment being in gaseous connection with an air inlet 14 formed in the assembly and an air outlet 32 in the mouthpiece when the device is assembled. This allows air to be drawn through the device by application of negative pressure, which is usually created by a user drawing air from the air outlet.

The cartridge 20 is a body which includes a vaporisable substance 22 and an induction heatable susceptor 24 (it is intended this susceptor may be the "second susceptor" referred to above). In this example the vaporisable substance includes one or more of tobacco, humectant, glycerine and propylene glycol. The susceptor is a plurality of plates that are electrically conducting. In this example, the cartridge also has a layer or membrane 26 to contain the vaporisable substance and susceptor, with the layer or membrane being air permeable. In other examples the membrane is not present.

As noted above, the induction heating assembly 10 is used to heat the cartridge 20. The assembly includes an induction heating device, in the form of an induction coil 16 and a power source 18. The power source and the induction coil are electrically connected such that electrical power may be selectively transmitted between the two components.

In this example the induction coil 16 is substantially cylindrical such that the form of the induction heating assembly 10 is also substantially cylindrical. The heating compartment 12 is defined radially inward of the induction coil with a base at an axial end of the induction coil and side walls around a radially inner side of the induction coil. The heating compartment is open at an opposing axial end of the induction coil to the base. When the vapour generating device 1 is assembled, the opening is covered by the mouthpiece 30 with an opening to the air outlet 32 being located at the opening of the heating compartment. In the example shown in the figures, the air inlet 14 has an opening into the heating compartment at the base of the heating compartment.

A temperature sensor 11 is also located at the base of the heating compartment 12. Accordingly, the temperature sensor is located within the heating compartment at the same axial end of the induction coil 16 as the base of the heating compartment. This means that when a cartridge 20 is located in the heating compartment and when the vapour generating device 1 is assembled (in other words when the vapour generating device is in use or ready for use) the cartridge is deformed around temperature sensor. This is because, in this example, the temperature sensor does not pierce the membrane 26 of the cartridge due to its size and shape.

The temperature sensor 11 is electrically connected to a controller 13 located within the induction heating assembly 10. The controller is also electrically connected to the induction coil 16 and the power source 18, and is adapted in use to control operation of the induction coil and the temperature sensor by determining when each is to be supplied with power from the power source.

As mentioned above, in order for vapour to be produced, the cartridge 20 is heated. This is achieved by an alternating electrical current changed from a direct electrical current supplied by the power source 18 to the induction coil 16. The current flows through the induction coil causing a controlled EM field to be generated in a region near the coil. The EM field generated provides a source for an external susceptor (in this case the susceptor plates of the cartridge) to absorb the EM energy and convert it to heat, thereby achieving induction heating.

In more detail, by power being provided to the induction coil 16 a current is caused to pass through the induction coil, causing an EM field to be generated. As mentioned above, the current supplied to the induction coil is an alternating (AC) current. This causes heat to be generated within the cartridge because, when the cartridge is located in the heating compartment 12, it is intended that the susceptor plates are arranged (substantially) parallel to the radius of the induction coil 16 as is shown in the figures, or at least have a length component parallel to the radius of the induction coil. Accordingly, when the AC current is supplied to the induction coil while the cartridge is located in the heating compartment, the positioning of the susceptor plates causes eddy currents to be induced in each plate due to coupling of the EM field generated by the induction coil to each susceptor plate. This causes heat to be generated in each plate by induction.

The plates of the cartridge 20 are in thermal communication with the vaporisable substance 22, in this example by direct or indirect contact between each susceptor plate and the vaporisable substance. This means that when the susceptor 24 is inductively heated by the induction coil 16 of the induction heating assembly 10, heat is transferred from the susceptor 24 to the vaporisable substance 22, to heat the vaporisable substance 22 and produce a vapour.

When the temperature sensor 11 is in use, it monitors the temperature by measuring temperature at its surface. Each temperature measurement is sent to the controller 13 in the form of an electrical signal.

When the vapour generating device 1 is in use, inducting heating provided by the inductive heating assembly 10 and temperature monitoring provided by the temperature sensor 11 are carried out in accordance with an example method.

According to the example method, when the vapour generating device 1 is in use, inductive heating is provided for a first period and temperature monitoring is carried out for a second period. The first and second periods are non-concurrent. Instead, the first and second periods occur at different times with the second period following the first period and the first period following the second period in a repeating cycle for the duration of a heating session during which monitoring of the temperature is required to provide controlled heating of the vaporisable substance 22. In different examples, a heating session might last just for the duration of a single puff (i.e. a single draw by the user on the mouthpiece), or it could, in alternative examples, last for multiple puffs and it could include a heat-up phase (or phases) and a maintain phase (or phases) and it could include transitions between different target temperatures, or other similar transitions.

Each cycle from the start of one period (either the first or second period) to the end of the other period (the other of the first or second period) has a duration of between about 0.05 seconds and about 0.15 seconds. In different examples, the second period is either the same length as, shorter than or longer than the first period.

In a further example, as well as the temperature being monitored, the controller adjusts the amount power provided to the induction coil 16 based on the temperature monitored by the temperature sensor 13. This is applied, for example, when there is a predetermined temperature to which the cartridge 20 is intended to be heated. The controller then increases or decreases the amount of power supplied to the induction coil based on the difference between the predetermined temperature and the monitored temperature to reduce the difference as much as possible.

In a similar example, heating is applied for a predetermined period of time on start-up of the device 1 in a new use session. The temperature sensor 13 is then used to monitor the temperature. The controller checks the monitored temperature against a look-up chart an adjusts the heating profile (so adjusts the amount of power being supplied to the induction coil 16 to adjust the amount of heating being provided) to compensate for the ambient temperature, condition of the capsule or to stop a session of use (such as if a predetermined amount of prior use of a capsule is detected, for instance by a predetermined rate of change of temperature). This allows the amount of power used to be reduced since normally the maximum amount of power it is possible to provide will be applied on start-up. However, this presents the greatest risk of overheating or burning, so monitoring is such a situation improves safety and reduces the possibility of damage to the components of the device.

Additionally in another example, the controller 13 averages a series of temperature measurements provided by the temperature sensor 11, with the series of temperature measurements being taken over a third period independent of the first and second periods. The averaged temperatures are then used in noise detection from which it is possible to filter out (i.e. remove) the noise from the electrical signal based on the noise detected from the averaged temperatures and/or to identify and discard or ignore unreliable or anomalous temperature measurements.

Figure 3:
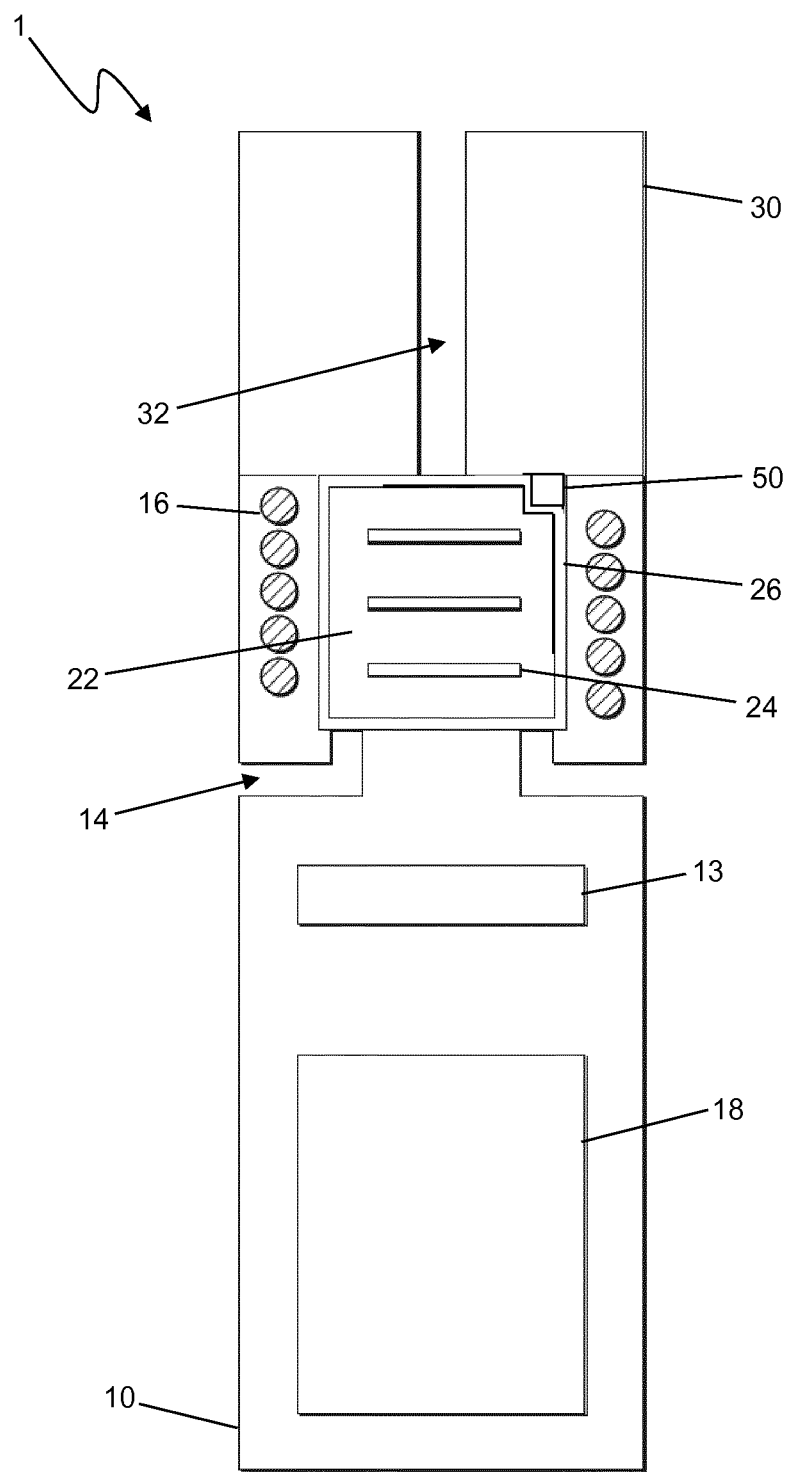
FIG. 3 shows a schematic view of a further example vapour generating device.

FIG. 3 shows a further example vapour generating device 1. In this further example, the vapour generating device has most of the same features as the vapour generating device shown in FIGS. 1 and 2. As such, the example vapour generating device 1 is a hand held device, which has an induction heating assembly 10, an induction heatable cartridge (which includes a vaporisable substance 22, an induction heatable susceptor 24 and, in this example, a membrane 26) and a mouthpiece 30.

The vapour generating device 1 of this example functions in the same way as described above in relation to the FIGS. 1 and 2. Accordingly, in use, air is drawn through air inlet 14, into the heating compartment containing the cartridge and out through the air outlet 32 in the mouthpiece 30 to the user.

As noted above, the induction heating assembly 10 is used to heat a cartridge. The assembly includes an induction heating device, in the form of an induction coil 16 and a power source 18. The power source and the induction coil are electrically connected such that electrical power may be selectively transmitted between the two components.

In the example shown in FIG. 3, no temperature sensor is shown. The temperature sensor may be present however and function as set out in relation to the example shown in FIGS. 1 and 2.

In the example shown in FIG. 3, there is an electronic component 50. This is an indicator located in the heating compartment of the heating assembly against a wall of the heating compartment where the mouthpiece 30 meets the heating compartment. This is therefore located at an end of the induction coil 16, close to the mouthpiece. This means when the induction coil is generating an EM field, the electronic component is located within the EM field.

In some examples, the electronic component 50 is configured to monitor remaining battery life. In other examples, the electronic component is configured to monitor the remaining lifespan of the cartridge, such as by monitoring the number of remaining draws of vapour available from the device, which corresponds to the remaining volume of vaporisable material. In further examples, the electronic component is configured to detect whether there is a cartridge present in the heating compartment.

The electronic component 50 contains a material that is able to act as a susceptor when exposed to an EM field. We have found that this causes the electronic component to operate in a manner other than the manner expected if operated when the induction coil 16 is operating due to the exposure to the EM field generated by the induction coil 16. This is due to the EM field causing interference in the material of the electronic component that is able to act as a susceptor. Note that in this context, when we say that the electronic component includes material that is able to act as a susceptor (i.e. the "first susceptor"), it does not necessarily imply that this material will generate significant heat, simply that it may be affected in some way by the electromagnetic field generated by the induction coil which can cause the electronic component to behave in an altered (and generally less optimum manner) when subjected to the influence of the electromagnetic field because of its susceptibility to the electromagnetic field. As such, when the vapour generation device 1 shown in FIG. 3 is in use, the electronic component and induction coil are operated during non-concurrent periods. This means the electronic component will only be active when there is no EM field being generated, thereby meaning there is no interference produced.

The invention claimed is:

1. An induction heating assembly for a vapour generating device, the heating assembly comprising:
   an induction heating device and an electronic component having material able to act as a first susceptor, wherein the induction heating device is arranged to heat, in use, a second susceptor for a first period, and the electronic component is arranged to be activated for a second period when the induction heating device is inactive such that no electromagnetic field is being generated by the induction heating device, and wherein the first period and the second period are non-concurrent.

2. The assembly according to claim 1, wherein the first and second periods are arranged to be sequential.

3. The assembly according to claim 1, wherein the first period is arranged to be repeated at least once and/or the second period is arranged to be repeated at least once.

4. The assembly according to claim 3, wherein each of the first and second periods is arranged to be repeated at least once and the first and second periods are arranged to alternate.

5. The assembly according to claim 1, wherein a time from a start of one of the first or second periods to an end of the other one of the first and second periods is arranged to be about 0.05 seconds to 0.15 seconds.

6. The assembly according to claim 1, wherein the electronic component is a temperature sensor, the temperature sensor being arranged to monitor, in use, a temperature related to heat generated from the second susceptor for the second period.

7. The assembly according to claim 6, wherein the induction heating device is arranged to adjust an amount of heat provided to the second susceptor based on the temperature monitored by the temperature sensor.

8. The assembly according to claim 6, further comprising a controller arranged in use to control the induction heating device and the temperature sensor.

9. The assembly according to claim 8, wherein the controller is arranged in use to control the induction heating device based on the temperature monitored by the temperature sensor.

10. The assembly according to claim 9, wherein the controller is arranged to control the induction heating device by being arranged in use to adjust an amount of power supplied to the induction heating device.

11. The assembly according to claim 8, wherein the controller is configured to average temperatures monitored by the temperature sensor over a third period so as to allow noise detection in the temperature monitored by the temperature sensor.

12. The assembly according to claim 11, wherein the controller is further configured to detect noise in the temperature monitored by the temperature sensor based on the averaged temperatures monitored during the third period and apply a filter to temperature monitored by the temperature sensor based on the detected noise so as to reduce noise in monitored temperatures.

13. The assembly according to claim 1, further comprising a power source arranged in use to provide power to the induction heating device and the electronic component.

14. A vapour generating device comprising:
    the induction heating assembly according to claim 1;
    a heating compartment arranged to receive a body comprising a vaporisable substance and an induction heatable susceptor;
    an air inlet arranged to provide air to the heating compartment; and
    an air outlet in communication with the heating compartment.

15. The assembly according to claim 1, wherein the induction heating device is an induction coil.

16. The assembly according to claim 1, wherein the electronic component is able to act as the first susceptor when exposed to an electromagnetic field from the heating device and wherein the electronic component is configured to only be active when no electromagnetic field is being generated.

17. A vapour generating device comprising:
- a body comprising a vaporisable substance and an induction heatable susceptor;
- a heating compartment arranged to receive the body;
- an air inlet arranged to provide air to the heating compartment;
- an air outlet in communication with the heating compartment; and
- an induction heating assembly including an induction coil and a temperature sensor having material able to act as a first susceptor, wherein the induction heating device is arranged to heat, in use, the induction heatable susceptor for a first period, and the temperature sensor is arranged to be activated for a second period when the induction heating device is inactive such that no electromagnetic field is being generated by the induction heating device, and wherein the first period and the second period are non-concurrent.

* * * * *